(12) United States Patent
Hiraike et al.

(10) Patent No.: US 7,098,355 B2
(45) Date of Patent: Aug. 29, 2006

(54) PROCESS FOR SYNTHESIS OF ORGANOMETALLIC COMPOUNDS

(75) Inventors: Hiroshi Hiraike, Osaka (JP); Takeharu Morita, Osaka (JP); Fumiyuki Ozawa, Osaka (JP); Hiroyuki Katayama, Osaka (JP)

(73) Assignee: Sekisui Chemical Co., Ltd., Osaka (JP)

( * ) Notice: Subject to any disclaimer, the term of this patent is extended or adjusted under 35 U.S.C. 154(b) by 92 days.

(21) Appl. No.: 10/489,604

(22) PCT Filed: Sep. 27, 2002

(86) PCT No.: PCT/JP02/10046

§ 371 (c)(1),
(2), (4) Date: Nov. 22, 2004

(87) PCT Pub. No.: WO03/029260

PCT Pub. Date: Apr. 10, 2003

(65) Prior Publication Data

US 2006/0030723 A1     Feb. 9, 2006

(30) Foreign Application Priority Data

Sep. 28, 2001  (JP)  .............................. 2001-301181
Jan. 22, 2002  (JP)  .............................. 2002-012333
Sep. 17, 2002  (JP)  .............................. 2002-270144

(51) Int. Cl.
*C07F 15/00* (2006.01)
*B01J 31/00* (2006.01)
*C08F 4/80* (2006.01)

(52) U.S. Cl. ........................ 556/22; 556/136; 556/137; 526/171; 502/155

(58) Field of Classification Search .................. 556/22, 556/136, 137; 526/171; 502/155
See application file for complete search history.

(56) References Cited

U.S. PATENT DOCUMENTS 6,306,987 B1 * 10/2001 Van Der Schaaf et al. . 526/171

FOREIGN PATENT DOCUMENTS

| JP | 11-262667 | 9/1999 |
|----|-----------|--------|
| JP | 11-510807 | 9/1999 |
| WO | WO 99/396 A1 | 1/1990 |
| WO | WO 97/6185 A1 | 2/1997 |

* cited by examiner

*Primary Examiner*—Porfirio Nazario-Gonzalez
(74) *Attorney, Agent, or Firm*—Armstrong, Kratz, Quintos, Hanson & Brooks, LLP

(57) ABSTRACT

A method for synthesizing an organometallic compound, which is usefully utilized as a catalyst for manufacturing polyolefins by ring-opening metathesis polymerization of an olefin having strain in a molecule such as dicyclopentadiene or synthesizing epothilones by ring-dosing metathesis reaction, by an efficient and low cost synthesis method using a starting material which is easily available due to relatively simple chemical structure, and further without any possibility of coexistence of a vinylhetero compound or a vinyl compound exchanged which tends to accompany as an impurity in the system in conventional methods, characterized by reacting a starting material comprising a zero-valent transition metal complex (A) or a polyvalent transition metal complex (A'), a compound (B) or (B') shown by the following general formula (1) or (4), respectively, and a neutral ligand (C) or (C'), in one step under non-reducing condition or reducing condition.

$$R^1Y^1CR^2X^1_2 \quad (1)$$

$$R^4Y^2CR^5X^2_2 \quad (4)$$

27 Claims, No Drawings

PROCESS FOR SYNTHESIS OF ORGANOMETALLIC COMPOUNDS

BACKGROUND OF THE INVENTION

1. Field of the Invention

The present invention relates to a method for synthesizing an organometallic compound, and in more detail, relates to an efficient and low cost method for synthesizing an organometallic compound usefully utilized as a catalyst for polyolefin manufacturing by ring-opening metathesis polymerization of an olefin having strain in a molecule such as dicyclopentadiene or synthesis of epothilones by ring-closing metathesis reaction, by using an easily available starting material due to relatively simple chemical structure.

2. Description of the Prior Art

A reaction using a transition metal compound has been utilized, by a catalytic action of a metal complex thereof, in wide fields ranging from synthesis of low molecular weight compounds such as medicines to synthesis of polymers such as highly functional plastics.

For example, polymerization of ethylene or propylene by Ziegler-Natta catalysts consisting of titanium tetrachloride or titanium trichloride and alkyl aluminum, polymerization to obtain uniform polyolefin by Kaminsky catalysts consisting of zirconocene and methylaluminoxane, organic metathesis reactions by transition metal carbene catalysts and the like, are well known.

Recently, transition metal carbene catalysts, in particular, ruthenium carbene catalyst is attracting attention. Ruthenium carbene catalyst is a compound having a Ru=C bond in a molecule (a bond between a ruthenium atom and divalent carbon atom without charge) and, in particular, dichloro-hydrogen-phenyl-carbene-bis(tri-cyclohexyl-phosphine)ruthenium, typically shown by [(Cl$_2$Ru=CHPh)(PCy$_3$)$_2$] has been developed by Grabs group of California Institute of technology and disclosed in JP-A-11-510807, JP-A-11-262667, and the like.

This compound has been found to show superior metathesis catalytic activity without deactivation even in the presence of moisture or oxygen and being not labile to a functional group in the metathesis reaction substrate, and utilized in ring-closing metathesis synthesis of various monomers useful as medicine and the like, or in manufacturing molded articles with superior mechanical strength, heat resistance, dimensional stability, and the like, by ring-opening polymerization of a norbornene type monomer, including dicyclopentadiene (hereinafter, may be abbreviated as DCPD), a typical monomer used in the metathesis polymerization, in a mold by a reactive injection molding method (hereinafter, may be abbreviated as RIM) and the like. Thus, the compound is used and attracts attention in various wide industrial fields.

However, since this catalyst is not activated in a reaction system with an alkyl metal and the like, but has an activity as a single complex, there is a problem that the reaction spontaneously starts as soon as the catalyst is added to a monomer with metathesis reactivity, and thereby dispersion of the catalyst and the like determines the reaction rate. This tendency may be a fatal problem in polymerization of a crosslinkable monomer such as dicyclopentadiene, it causes problems such as serious limitation on a process or variation of physical properties of a polymer obtained.

To overcome this problem, a method of adding triphenylphosphine or the like to a reaction system to retard polymerization is generally known. However, it also has a problem of product safety due to contamination of impurities such as phosphorus in the system.

As a catalyst to solve the above-described problems, dichloro-hydrogen-phenyl-thio-carbene-bis(tri-cyclohexyl-phosphine)ruthenium, typically shown by [(Cl$_2$Ru=CHSPh)(PCy$_3$)$_2$] has been disclosed in WO 99/00396. This patent also discloses such compounds whose sulfur atom is substituted with an oxygen atom, an imino group or a phosphine-di-yl group, in the above-described chemical formula of this catalyst.

This catalyst is very superior, but a synthesis method thereof, as shown in a) and b) of Example 1 in the page 33 of said official gazette, has problems. Namely, in the case of a), a raw material itself has a complicated chemical structure such as RuCl$_2$[P(C$_6$H$_{11}$)$_3$]$_2$(=CH—CrH$_5$), and thus requires many steps in preparation, while in the case of b), a raw material, ruthenium dichloride(cis,cis-cyclopentadiene), although the chemical structure itself is simple, must be reacted with 1,8-diazabicyclo[5.4.0]undeca-7-ene and tricyclohexylphosphine, both having complicated chemical structures, in isopropanol at 80° C. for 1 hour, followed by reacting at −20° C. for 1 hour, further adding 1 mole of a solution of diethyl ether hydrochloride, stirring for 15 minutes and further adding 1-hexyne and phenyl vinyl sulfide, to synthesize the target substance, thus requiring use of many expensive raw materials and making the synthesis complicated with many reaction steps as well as disadvantageous in cost.

A method for synthesizing a hetero carbene complex such as RuCl$_2$[P(C$_6$H$_{11}$)$_3$]$_2$(=CH—S—) generally includes, for example, as shown in "Chemistry. Letters", 1999, 369 or "Organometallics", 2002, 21, 2153–2164, a reaction of a conventional alkylidene complex with a vinylhetero compound such as vinyl sulfide, followed by exchanging a vinyl moiety. However, heteroalkylidene complexes synthesized by these synthesis methods have a residual vinylhetero compound from the raw material or a vinyl compound exchanged due to co-existence in the system, and it is generally known that the complex synthesized inhibits the metathesis reaction by these remaining compounds.

Therefore, in the method for synthesizing a hetero carbene complex by the vinyl exchange requires complete removal of these vinyl compounds from the system. To solve such problems, it is necessary to repeat a washing step many times after isolation. However, additional unnecessary washing step or accompanying decrease in yield is not preferable from the industrial point of view.

SUMMARY OF THE INVENTION

In consideration of the above-described problems, an object of the present invention is to provide an efficient and low cost method for synthesizing an organometallic compound usefully utilized as a catalyst for polyolefin manufacturing by ring-opening metathesis polymerization of an olefin having strain in a molecule such as dicyclopentadiene or synthesis of epothilones by ring-dosing metathesis reaction, by using easily available starting materials due to relatively simple chemical structure. Further, another object of the present invention is to provide a method for simply isolating an organometallic compound having high activity from a reaction solution, with no possibility of co-existence of a vinylhetero compound or a vinyl compound exchanged in a system, which tends to accompany as an impurity in the conventional methods.

The present inventors have found, after-comprehensive study to solve the problems of the conventional synthesis methods for an organometallic compound, that a target organometallic compound can be synthesized efficiently even in high yield and in low cost, from a transition metal complex having a relatively simple chemical structure and easily available, as a starting substance, by reacting with a halogenated methane containing a chalcogen hydrocarbon group having a simple chemical structure and a neutral ligand in one step, and further that it is possible to simply isolate an organometallic compound having high activity from a reaction solution, with no possibility of co-existence of a vinyl hetero compound or a vinyl compound exchanged in the system which tends to accompany as an impurity in the conventional methods, and thus have completed the present invention.

The first aspect of the present invention provides a method for synthesizing an organometallic compound characterized by reacting a starting material comprising a zero-valent transition metal complex (A), a compound (B) shown by the following general formula (1) and a neutral ligand (C) in one step (hereinafter, referred to the first manufacturing method):

$$R^1Y^1CR^2X^1_2 \quad (1)$$

(wherein $R^1$ is a hydrogen atom, an alkyl group having 1 to 20 carbon atoms, an alkenyl group having 2 to 20 carbon atoms or an aryl group having 6 to 20 carbon atoms, which may be substituted with an alkyl group having 1 to 5 carbon atoms, a carboxyl group, an alkoxy group having 1 to 5 carbon atoms, an alkenyloxy group having 1 to 5 carbon atoms, an aryloxy group having 6 to 10 carbon atoms, an alkylsilyl group having 1 to 6 carbon atoms, an arylsilyl group having 6 to 10 carbon atoms, an acyl group having 1 to 7 carbon atoms, a hydroxyl group, an amino group having 0 to 10 carbon atoms, a halogen atom, a nitro group, an acetyl group or an acetoxy group; $Y^1$ is a chalcogen atom or a nitrogen-containing group shown by the following formula (2):

$$\begin{array}{c} -N- \\ | \\ R^3 \end{array} \quad (2)$$

or a phosphorus-containing group shown by the following formula (3):

$$\begin{array}{c} -P- \\ | \\ R^3 \end{array} \quad (3)$$

and $X^1$ is a halogen atom. $R^2$ and $R^3$ in the formula have the same definition as $R^1$, and any pair of $R^1$, $R^2$ or $R^3$ may be bonded each other) is provided.

The second aspect of the present invention provides a method for synthesizing an organometallic compound characterized by reacting a starting material comprising a polyvalent transition metal complex (A') and a compound (B') shown by the following general formula (4):

$$R^4Y^2CR^5X^2_2 \quad (4)$$

(wherein $R^4$, $R^5$, $Y^2$ and $X^2$ have respectively the same definitions as the above-described $R^1$, $R^2$, $Y^1$ and $X^1$. Any pair of $R^3$, $R^4$ or $R^5$ may be bonded each other) and a neutral ligand (C') in one step under reducing condition (hereinafter, referred to the second manufacturing method) is provided.

The third aspect of the present invention provides a method for synthesizing an organometallic compound characterized by that, in the first aspect, said transition metal complex (A) has an arene ligand and an olefin ligand, is provided.

The fourth aspect of the present invention, a method for synthesizing an organometallic compound characterized by that, in the third aspect, said olefin ligand is a cyclic olefin ligand, is provided.

The fifth aspect of the present invention, a method for synthesizing an organometallic compound characterized by that, in the second aspect, said transition metal complex (A') has an arene ligand, is provided.

The sixth aspect of the present invention, a method for synthesizing an organometallic compound characterized by that, in the first or the second aspect, a central metal of said transition metal complex (A) or (A') is a transition metal of VIA group, VIIA group, VIII group or IB group, is provided.

The seventh aspect of the present invention, a method for synthesizing an organometallic compound characterized by that, in the sixth aspect, the central metal of said transition metal complex (A) or (A') is ruthenium or osmium, is provided.

The eighth aspect of the present invention, a method for synthesizing an organometallic compound characterized by that, in the first or the second aspect, $R^2$ or $R^5$ in said formula is a hydrogen atom, is provided.

The ninth aspect of the present invention, a method for synthesizing an organometallic compound characterized by that, in the first or the second aspect, $R^1$, $R^3$ or $R^4$ in said formula is a phenyl group or a phenyl group substituted with at least one substituent selected from a group consisting of an alkyl group having 1 to 5 carbon atoms, a carboxyl group, an alkoxy group having 1 to 5 carbon atoms, an alkenyloxy group having 1 to 5 carbon atoms, an aryloxy group having 6 to 10 carbon atoms, an alkylsilyl group having 1 to 6 carbon atoms, an arylsilyl group having 6 to 10 carbon atoms, an acyl group having 1 to 7 carbon atoms, a hydroxyl group, an amino group having not more than 10 carbon atoms, a halogen atom, a nitro group and an acetyl group, is provided.

The tenth aspect of the present invention, a method for synthesizing an organometallic compound characterized by that, in the first or the second aspect, $Y^1$ or $Y^2$ in said formula is an oxygen atom, a sulfur atom or a selenium atom, is provided.

The eleventh aspect of the present invention, a method for synthesizing an organometallic compound characterized by that, in the first or the second aspect, said neutral ligand (C) or (C') is a tertiary phosphine or an imidazolium-2-ylidene compound, is provided.

The twelfth aspect of the present invention, a method for synthesizing an organometallic compound characterized by that, in the second aspect, said reducing condition is realized by using a reducing agent, is provided.

The thirteenth aspect of the present invention, a method for synthesizing an organometallic compound characterized by that, in the twelfth aspect, said reducing agent is a typical element or a compound containing the typical element, is provided.

The fourteenth aspect of the present invention, a method for synthesizing an organometallic compound characterized by that, in the thirteenth aspect, said reducing agent is zinc, is provided.

The fifteenth aspect of the present invention, a method for synthesizing an organometallic compound characterized by that, in the thirteenth aspect, said reducing agent is a sodium compound, is provided.

The sixteenth aspect of the present invention, a method for synthesizing an organometallic compound characterized by that, in the second aspect, an alcohol further coexists as a reducing auxiliary, is provided.

The seventeenth aspect of the present invention, a method for synthesizing an organometallic compound characterized by that, in the second aspect, an olefin compound is further coexists as a reducing auxiliary, is provided.

The eighteenth aspect of the present invention, a method for synthesizing an organometallic compound characterized by that, in the seventeenth aspect, said olefin compound is a cyclic olefin, is provided.

The nineteenth aspect of the present invention, a method for synthesizing an organometallic compound characterized by that, in the first aspect, said organometallic compound is a compound shown by the following general formula (5):

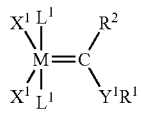

(5)

(wherein M is a transition metal element; $R^1$, $R^2$, $Y^1$ and $X^1$ have each the same definition as described above. Two $L^1$s may be the same or different each other and are neutral electron donors), is provided.

The twentieth aspect of the present invention, a method for synthesizing an organometallic compound characterized by that, in the second aspect, said organometallic compound is a compound shown by the following general formula (6):

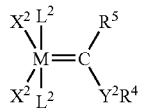

(6)

(wherein M is a transition metal element; $R^4$, $R^5$, $Y^2$ and $X^2$ have each the same definition as described above. Two $L^2$s may be the same or different each other and are neutral electron donors), is provided.

The twenty-first aspect of the present invention, a method for synthesizing an organometallic compound characterized by that, in the nineteenth or twentieth aspect, M in said formula is ruthenium or osmium, is provided.

The twenty-second aspect of the present invention, a method for synthesizing an organometailic compound characterized by that, in the nineteenth or twentieth aspect, $R^2$ or $R^5$ in said formula is a hydrogen atom, is provided.

The twenty-third aspect of the present invention, a method for synthesizing an organometallic compound characterized by that, in the nineteenth or twentieth aspect, $R^1$, $R^3$ or $R^4$ in said formula is a phenyl group or a phenyl group substituted with at least one substituent selected from a group consisting of an alkyl group having 1 to 5 carbon atoms, a carboxyl group, an alkoxy group having 1 to 5 carbon atoms, an alkenyloxy group having 1 to 5 carbon atoms, an aryloxy group having 6 to 10 carbon atoms, an alkylsilyl group having 1 to 6 carbon atoms, an arylsilyl group having 6 to 10 carbon atoms, an acyl group having 1 to 7 carbon atoms, a hydroxyl group, an amino group having not more than 10 carbon atoms, a halogen atom, a nitro group and an acetyl group, is provided.

The twenty-fourth aspect of the present invention, a method for synthesizing an organometallic compound characterized by that, in the nineteenth or twentieth aspect, $Y^1$ or $Y^2$ in said formula is an oxygen atom, a sulfur atom or a selenium atom, is provided.

The twenty-fifth aspect of the present invention, a method for synthesizing an organometallic compound characterized by that, in the first aspect, said organometallic compound is dichloro [bis(tricyclohexylphosphino)]phenyl thio methyno ruthenium, is provided.

The twenty-sixth aspect of the present invention, a method for synthesizing an organometallic compound characterized by that, in the first aspect, said zero-valent transition metal complex (A) is ($\eta^6$-p-cymene)($\eta^4$-1,5-cyclooctadiene)ruthenium(0), is provided.

The twenty-seventh aspect of the present invention, a method for synthesizing an organometallic compound characterized by that, in the first aspect, said organometallic compound does not contain an impurity of a vinylhetero compound or a vinyl compound, is provided.

DETAILED DESCRIPTION OF THE INVENTION

Hereinbelow, the method for synthesizing an organometallic compound of the present invention will be described in detail item by item.

1. Transition Metal Complexes (A) and (A')

The transition metal complex (A) or (A') used in the first or second manufacturing method of the present invention is one of raw materials for an organometallic compound which is a target product of the present invention, and each of them plays a role to provide a metal complex in an organometallic compound.

In the first manufacturing method, a zero-valent metal complex is used as a transition metal complex (A), while in the second manufacturing method, a polyvalent metal complex is used as a transition metal complex (A'). Therefore, in the first manufacturing method where a zero-valent transition metal complex (A) is used, a target substance can be obtained without adding a reducing agent, while in the second manufacturing method where a polyvalent transition metal complex (A') is used, a target substance cannot be obtained in good yield unless the reaction is carried out under reducing condition by adding a reducing agent.

The central metal of transition metal complexes (A) and (A') is not particularly limited as long as it forms a transition metal complex, but a transition metal of VIA group, VIIA group, VIII group or IB group is preferable. Ruthenium or osmium, in particular, is desirable among others in view of reactivity and usefulness.

The ligand used in transition metal complexes (A) and (A') is not particularly limited as long as it forms a transition metal complex.

Among these ligands, in the case of a zero-valent transition metal complex (A), combined use of an arene ligand and an olefin ligand is preferable in view of stability and reactivity of the complex.

In this case, the arene ligand described above desirably includes, for example, benzene and derivatives thereof such as toluene, cumene, cymene, hexamethylbenzene and benzoate esters, and naphthalene.

The olefin ligand includes a monoolefin such as ethylene, dienes such as butadiene, cyclohexadiene and trienes such as cyclooctatriene. As the monoolefin, bimolecular coordination is desirable in view of saturated electron quantity.

A cycloolefin is more desirable in view of both stability and reactivity of the complex. Specific examples include cyclodiene such as 1,3-cyclohexadiene, 1,4-cyclohexadiene, 1,3-cyclooctadiene, 1,5-cyclooctadiene and α-terpinene, or substituted compounds of these cycloolefins and cyclotriene such as 1,3,5-cyclooctatriene and 1,3,5-cycloheptatriene. Among others, cyclodiene is preferable in view of stability of the complex.

In the case of a polyvalent transition metal complex (A'), use of an arene ligand is desirable in view of both stability and reactivity of the complex.

In this case, the arene ligand described above desirably includes, for example, benzene and derivatives thereof such as toluene, cumene, cymene, hexamethylbenzene and benzoate esters, and naphthalene.

The zero-valent transition metal complex (A) includes, for example, the following, wherein valence and chemical formula of each complex are shown in ( ) and [ ], respectively.

1. dodecacarbonyltriruthenium(0), $[Ru_3(CO)_{12}]$
2. tricarbonyl(cyclooctatriene)ruthenium(0), $[Ru(CO)_3(\eta^6\text{-}1,3,5\text{-}C_8H_{10})]$
3. tricarbonyl(1,5-cyclooctadiene)ruthenium(0), $[Ru(CO)_3(\eta^4\text{-}1,5\text{-}C_8H_{12})]$
4. ($\eta^6$-1,3,5-cyclooctatriene)($\eta^4$-1,5-cyclooctadiene)ruthenium(0), $[Ru(\eta^6\text{-}1,3,5\text{-}C_8H_{10})(\eta^4\text{-}1,5\text{-}C_8H_{12})]$
5. ($\eta^6$-benzene)($\eta^4$-1,3-cyclohexadiene)ruthenium(0), $[Ru(\eta^6\text{-}C_6H_6)(\eta^4\text{-}1,3\text{-}C_6H_8)]$
6. ($\eta^6$-benzene)($\eta^4$-1,5-cyclooctadiene)ruthenium(0), $[Ru\{\eta^6\text{-}C_6H_6\}(\eta^4\text{-}1,5\text{-}C_8H_{12})]$
7. ($\eta^6$-cymene)($\eta^4$-1,5-cyclooctadiene)ruthenium(0), $[Ru\{\eta^6\text{-}CH(CH_3)_2C_6H_4CH_3\}(\eta^4\text{-}1,5\text{-}C_8H_{12})]$
8. ($\eta^6$-naphthalene)($\eta^4$-1,5-cyclooctadiene)ruthenium(0), $[Ru(\eta^6\text{-}C_{10}H_{10})(\eta^4\text{-}1,5\text{-}C_8H_{12})]$
9. ($\eta^6$-cymene)($\eta^4$-α-terpinene)ruthenium(0), $[Ru(\eta^6\text{-}CH(CH_3)_2C_6H_4CH_3)(\eta^4\text{-}\alpha\text{-Terpinene})]$
10. ($\eta^6$-cymene)bis(ethylene)ruthenium(0), $[Ru\{\eta^6\text{-}CH(CH_3)_2C_6H_4CH_3\}(C_2H_4)_2]$
11. ($\eta^6$-cymene)($\eta^4$-1,3-cyclohexadiene)ruthenium(0), $[Ru\{\eta^6\text{-}CH(CH_3)_2C_6H_4CH_3\}(\eta^4\text{-}1,3\text{-}C_6H_8)]$
12. ($\eta^6$-ethyl benzoate)($\eta^4$-1,5-cyclooctadiene)ruthenium(0), $[Ru\{\eta^6\text{-}C_6H_5COOEt\}(\eta^4\text{-}1,5\text{-}C_8H_{12})]$
13. ($\eta^6$-hexamethylbenzene)($\eta^4$-1,5-cyclooctadiene) ruthenium(0), $[Ru\{\eta^6\text{-}C_6Me_6\}(\eta^4\text{-}1,5\text{-}C_8H_{12})]$
14. bis($\eta^6$-hexamethylbenzene)ruthenium(0), $[Ru\{\eta^6\text{-}C_6(CH_3)_6\}_2]$
15. dodecacarbonyltriosmium(0), $[Os_3(CO)_{12}]$
16. η-decacarbonyldihydridetriosmium(0), $[Os_3H_2(CO)_{10}]$
17. undecacarbonyl(acetonitrile)triosmium(0), $[Os_3(CO)_{11}(CH_3CN)]$
18. ($\eta^6$-benzene)($\eta^4$-1,3-cyclohexadiene)osmium(0), $[Os(\eta^6\text{-}C_6H_6)(\eta^4\text{-}1,3\text{-}C_6H_8)]$
19. ($\eta^6$-benzene)($\eta^4$-1,5-cyclooctadiene)osmium(0), $[Os(\eta^6\text{-}C_6H_6)(\eta^4\text{-}1,5\text{-}C_8H_{12})]$
20. ($\eta^6$-cymene)($\eta^4$-1,5-cyclooctadiene)osmium(0), $[Os\{\eta^6\text{-}CH(CH_3)_2C_6H_4CH_3\}(\eta^4\text{-}1,5\text{-}C_8H_{12})]$
21. ($\eta^6$-naphthalene)($\eta^4$-1,5-cyclooctadiene)osmium(0), $[Os(\eta^6\text{-}C_{10}H_{10})(\eta^4\text{-}1,5\text{-}C_8H_{12})]$
22. ($\eta^6$-benzene)($\eta^4$-α-terpinene)osmium(0), $[Os(\eta^6\text{-}C_6H_6)(\eta^4\text{-}\alpha\text{-Terpinene})]$
23. ($\eta^6$-cymene)bis(ethylene)osmium(0), $[Os\{\eta^6\text{-}CH(CH_3)_2C_6H_4CH_3\}(C_2H_4)_2]$
24. ($\eta^6$-ethyl benzoate)($\eta^4$-1,5-cyclooctadiene)osmium(0), $[Os\{\eta^6\text{-}C_6H_5COOEt\}(\eta^4\text{-}1,5\text{-}C_8H_{12})]$
25. ($\eta^6$-hexamethylbenzene)($\eta^4$-1,5-cyclooctadiene)osmium(0), $[OS(\eta^6\text{-}C_6Me_6)(\eta^4\text{-}1,5\text{-}C_8H_{12})]$ Among the above-described zero-valent transition metal complexes (A), a preferable one in view of stability and manufacturing cost of the complex includes
($\eta^6$-1,3-cyclooctatriene)($\eta^4$-1,5-cyclooctadiene)ruthenium(0),
($\eta^6$-benzene) ($\eta^4$-cyclohexadiene)ruthenium(0),
($\eta^6$-benzene)($\eta^4$-1,5-cyclooctadiene)ruthenium(0),
($\eta^6$-cymene)($\eta^4$-1,5-cyclooctadiene)ruthenium(0) and
($\eta^6$-naphthalene)($\eta^4$-1,5-cyclohexadiene)ruthenium(0), and among others, a more preferable one includes ($\eta^6$-benzene)($\eta^4$-cyclohexadiene)ruthenium(0) and ($\eta^6$-cymene)($\eta^4$-1,5-cyclooctadiene)ruthenium(0).

The polyvalent transition metal complex (A'), on the other hand, includes, for example, the following, wherein valence and chemical formula of each complex are shown in ( ) and [ ], respectively.

1. di-μ-chlorobis(chlorotricarbonylruthenium(II), $[RuCl_2(CO)_3]_2$
2. bis($\eta^5$-cyclopentadienyl)ruthenium(II), $[Ru(\eta^5\text{-}C_5H_5)_2]$
3. bis($\eta^5$-pentamethylcyclopentadienyl)ruthenium(II), $[Ru\{\eta^5\text{-}C_5(CH_3)_5\}_2]$
4. ($\eta^5$-cyclopentadienyl)($\eta^5$-pentamethylcyclopentadienyl)ruthenium(II), $[Ru(\eta^5\text{-}C_5H_5)\{\eta^5\text{-}C_5(CH_3)_5\}]$
5. tetracarbonylbis($\eta^5$-cyclopentadienyl)diruthenium(I), $[Ru_2(CO)_4(\eta^5\text{-}C_5H_5)_2]$
6. tetracarbonylbis($\eta^5$-pentamethylcyclopentadienyl) diruthenium(I), $[Ru_2(CO)_4\{\eta^5\text{-}C_5(CH_3)_5\}_2]$
7. dichlorobis($\eta^5$-pentamethylcyclopentadienyl) ruthenium (III), $[RuCl_2\{\eta^5\text{-}C_5(CH_3)_5\}_2]$
8. chlorodicarbonyl($\eta^5$-cyclopentadienyl)ruthenium(II), $[RuCl\{\eta^5\text{-}C_5H_5\}(CO)_2]$
9. hydride($\eta^5$-cyclopentadienyl)($\eta^5$-cyclooctadienyl) ruthenium(II), $[RuH(\eta^5\text{-}C_5H_5)(\eta^8\text{-}C_8H_{12})]$
10. chloro($\eta^5$-cyclopentadienyl)($\eta^8$-cyclooctadienyl) ruthenium(II), $[RuCl(\eta^5\text{-}C_5H_5)(\eta^8\text{-}C_8H_{12})]$
11. bromo($\eta^5$-cyclopentadienyl)($\eta^8$-cyclooctadienyl) ruthenium(II), $[RuBr(\eta^5\text{-}C_5H_5)(\eta^8\text{-}C_8H_{12})]$
12. chlorodicarbonyl($\eta^5$-pentamethylcyclopentadienyl) ruthenium(II), $[RuCl(CO)_2\{\eta^5\text{-}C_5(CH_3)_5\}]$
13. iododicarbonyl($\eta^5$-pentamethylcyclopentadienyl) ruthenium(II), $[RuI(CO)_2(\eta^5\text{-}C_5(CH_3)_5\}]$
14. chloro($\Theta^5$-pentamethylcyclopentadienyl)($\eta^4$-1,5-cyclooctadienyl) ruthenium(II), $[RuCl\{\eta^5\text{-}C_5(CH_3)_5\}(\eta^4\text{-}1,5\text{-}C_8H_{12})]$
15. trichloro($\eta^5$-pentamethylcyclopentadienyl)ruthenium (IV), $[RuCl_3\{\eta^5\text{-}C_5(CH_3)_5\}]_2$
16. dichloro($\eta^3$-allyl)($\eta^5$-pentamethylcyclopentadienyl) ruthenium(IV), $[RuCl_2(\eta^3\text{-}C_3H_5)\{\eta^5\text{-}C_5(CH_3)_5\}]$
17. tetrachlorobis($\eta^6$-benzene)diruthenium(III), $[RuCl_2(\eta^6\text{-}C_6H_6)]_2$
18. tetrachlorobis($\eta^6$-hexamethylbenzene)diruthenium(II), $[RuCl_2\{\eta\text{ }6\text{-}C_6(CH_3)_6\}]_2$
19. bis($\eta^3$-allyl) ($\eta^4$-norbornadiene)diruthenium(II), $[Ru(\eta^3\text{-}C_3H_5)(\eta^4\text{-}C_7H_8)]_2$
20. tetrachlorobis($\eta^6$-cymene)diruthenium(II), $[RuCl_2\{\eta^6\text{-}CH(CH_3)_2C_6H_4CH_3\}]_2$
21. tetrachlorobis($\eta^6$-ethyl benzoate)diruthenium(II), $[RuCl_2\{\eta^6\text{-}C_6H_5COOEt\}]_2$
22. dichloro($\eta^4$-1,5-cyclooctadiene) ruthenium(II), $[RuCl_2(\eta^4\text{-}1,5\text{-}C_8H_{12})]_2$
23. trichlororuthenium(III)trihydrate, $[RuCl_3\cdot3H_2O]$
24. bis($\eta^5$-cyclopentadienyl)osmium (II), $[Os(\eta^5\text{-}C_5H_5)_2]$
25. bis($\eta^5$-pentamethylcyclopentadienyl)osmium (II), $[Os\{\eta^5\text{-}C_5(CH_3)_5\}_2]$
26. ($\eta^5$-acethylcyclopentadienyl)($\eta^5$-cyclopentadienyl)osmium (II), $[Os(\eta^5\text{-}C_5H_5)(\eta^5\text{-}C_5H_4COCH_3)]$ 27. tetrachlorobis($\eta^6$-benzene)diosniium (II), [OsCl$_2$($\eta^6$-C$_6$H$_6$)]$_2$
28. tetrachlorobis($\eta^6$-hexamethylbenzene)diosmium (II), [OsCl$_2$($\eta^6$-C$_6$(CH$_3$)$_6$)]$_2$
29. tetrachlorobis($\eta^6$-cymene)diosmium (II), [OsCl$_2$\{$\eta^6$-CH(CH$_3$)$_2$C$_6$H$_4$CH$_3$\}]$_2$
30. tetrachlorobis($\eta^6$-ethyl benzoate)diosmium(II), [OsCl$_2$\{$\eta^6$-C$_6$H$_5$COOEt\}]$_2$ 2. Compounds (B) and (B')

Each of the compound (B) and (B') used in the first and the second manufacturing method of the present invention is one of raw materials for the organometailic compound which is a target product of the present invention, and each of them plays a role to provide an anionic ligand such as a halogen group directly bonding to a metal in the organometallic compound, and an electron donor group such as a phenylthio group and a phenyl ether group directly bonding to carbene (a divalent carbon atom without charge) in the organometallic compound.

In the first manufacturing method, a compound shown by the following general formula (1) is used as the compound (B):

$$R^1Y^1CR^2X^1_2 \quad (1)$$

(wherein $R^1$ is a hydrogen atom, an alkyl group having 1 to 20 carbon atoms, an alkenyl group having 2 to 20 carbon atoms or an aryl group having 6 to 20 carbon atoms, and these groups may be substituted with an alkyl group having 1 to 5 carbon atoms, a carboxyl group, an alkoxy group having 1 to 5 carbon atoms, an alkenyloxy group having 1 to 5 carbon atoms, an aryloxy group having 6 to 10 carbon atoms, an alkylsilyl group having 1 to 6 carbon atoms, an arylsilyl group having 6 to 10 carbon atoms, an acyl group having 1 to 7 carbon atoms, a hydroxyl group, an amino group having 0 to 10 carbon atoms, a halogen group, a nitro group, an acetyl group or an acetoxy group; $Y^1$ is a chalcogen atom or a nitrogen-containing group shown by the following formula (2):

or a phosphorus-containing group shown by the following formula (3):

and $X^1$ is a halogen atom. $R^2$ and $R^3$ in the formula have the same definition as $R^1$, and $R^1$, $R^2$ or $R^3$ may be bonded each other).

In the second manufacturing method, a compound shown by the following general formula (4) is used as the compound (B'):

$$R^4Y^2CR^5X^2_2 \quad (4)$$

(wherein $R^4$, $R^5$, $Y^2$ and $X^2$ have respectively the same definitions as the above-described $R^1$, $R^2$, $Y^1$ and $X^1$. $R^3$, $R^4$ or $R^5$ may be bonded each other).

Each of the compounds (B) and (B') of the present invention is not particularly limited as long as it belongs to those shown by the above-described general formula (1) or the general formula (4), but a preferable one includes, in view of reactivity and usefulness, a compound whose $R^2$ or $R^5$ in the formula is a hydrogen atom, and further, a particularly preferable one is a compound whose $R^1$, $R^3$ or $R^4$ in the formula is a phenyl group or a phenyl group substituted with at least one substituent selected from a group consisting of an alkyl group having 1 to 5 carbon atoms, a carboxyl group, an alkoxy group having 1 to 5 carbon atoms, an alkenyloxy group having 1 to 5 carbon atoms, an aryloxy group having 6 to 10 carbon atoms, an alkylsilyl group having 1 to 6 carbon atoms, an arylsilyl group having 6 to 10 carbon atoms, an acyl group having 1 to 7 carbon atoms, a hydroxyl group, an amino group having not higher than 10 carbon atoms, a halogen group, a nitro group and an acetyl group; and $Y^1$ or $Y^2$ is an oxygen atom, a sulfur atom or a selenium atom.

Specific examples of the compounds (B) and (B') used in the present invention include, for example, the following, wherein chemical formula of each complex is shown in [ ].

1. dichloromethylphenylsulfide, [Ph—S—CHCl$_2$]
2. dichloromethylphenylselenide, [Ph—Se—CHCl$_2$]
3. dichloromethylphenylphosphine, [Ph-PH—CHCl$_2$]
4. dichloromethylphenylamine, [Ph-NH—CHCl$_2$]
5. (phenyldichloromethyl)phenylsulfide, [Ph—S—C(Ph)Cl$_2$]
6. dichloromethyl-p-tolylsulfide, [p-tolyl-S—CHCl$_2$]
7. dichloromethyl-p-tolylselenide, [p-tolyl-Se—CHCl$_2$]
8. dichloromethyl-p-tolylphosphine, [p-tolyl-PH—CHCl$_2$]
9. dichloromethyl-p-tolylamine, [p-tolyl-NH—CHCl$_2$]
10. dichloromethyl-p-chlorophenylsulfide, [p—Cl-Ph—S—CHCl$_2$]
11. dichloromethyl-p-chlorophenylselenide, [p-Cl-Ph—Se—CHCl$_2$]
12. dichloromethyl-p-chlorophenylphosphine, [p—Cl-Ph-PH—CHCl$_2$]
13. dichloromethyl-p-chlorophenylamine, [p-Cl-Ph-NH—CHCl$_2$]
14. dichloromethyl-p-methoxyphenylsulfide, [p-MeO-Ph—S—CHCl$_2$]
15. dichloromethyl-p-methoxyphenylselenide, [p-MeO-Ph—Se—CHCl$_2$]
16. dichloromethyl-p-methoxyphenylphosphine, [p-MeO-Ph-PH—CHCl$_2$]
17. dichloromethyl-p-methoxyphenylamine, [p-MeO-Ph-NH—CHCl$_2$]
18. dichloromethylbenzylselenide, [Benzyl-Se—CHCl$_2$]
19. dichloromethylisopropylsulfide, [i-Pr—S—CHCl$_2$]
20. dichloromethylisopropylselenide, [i-Pr—Se—CHCl$_2$]
21. dichloromethylisopropylphosphine, [i-Pr—PH—CHCl$_2$]
22. dichloromethylisopropylamine, [i-Pr—NH—CHCl$_2$]
23. N-dichloromethylcarbazole,

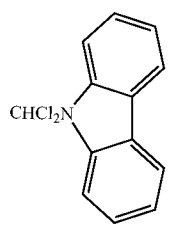

24. N-dichloromethylpyrrolidinone,

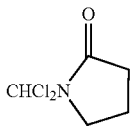

25. N-dichloromethylphthalmide,

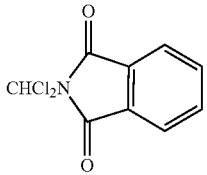

26. N-dichloromethylpyrrolidine,

3. Neutral Ligands (C) and (C')

Each of the neutral ligands (C) and (C') used in the first and the second manufacturing method of the present invention is a neutral electron donor and one of raw materials for the organometallic compound which is a target product of the present invention, and each of them plays a role to provide a neutral ligand directly bonding to a metal in the organometallic compound.

Any type of the neutral ligands (C) and (C') can be used as long as it is a neutral electron donor, but tertiary phosphine or an imidazolium-2-ylidene compound is preferable.

The tertiary phosphine includes a phosphine shown by the formula $PR^6R^7R^8$, wherein each of $R^6$, $R^7$ and $R^8$ independently shows an alkyl group having 1 to 20 carbon atoms or an aryl group having 6 to 20 carbon atoms, and preferably a group selected from a methyl group, an ethyl group, an isopropyl group, a tert-butyl group, a cyclohexyl group, a phenyl group and a substituted phenyl group, and they may be the same each other.

As the tertiary phosphine, a bidentate type phosphine such as bisphosphine can be used.

A specific example of the tertiary phosphine used in the present invention includes, for example, the following, wherein chemical formula of each complex is shown in [ ].
1. tricyclopentylphosphine, $[P(C_5H_9)_3]$
2. tricyclohexylphosphine, $[P(C_6H_{11})_3]$
3. tricyclooctylphosphine, $[P(C_8H_{15})_3]$
4. triethylphosphine, $[P(C_2H_5)_3]$
5. trimethylphosphine, $[P(CH_3)_3]$
6. triisopropylphosphine, $[P\{CH(CH_3)_2\}_3]$
7. tripropylphosphine, $[P(CH_2CH_2CH_3)_3]$
8. tributylphosphine, $[P(CH_2CH_2CH_2CH_3)_3]$
9. dimethylethylphosphine, $[P(CH_3)_2C_2H_5]$
10. methyldiethylphosphine, $[PCH_3(C_2H_5)_2]$
11. triphenethylphosphine, $[P(CH_2CH_2Ph)_3]$
12. tributoxyethylphosphine, $[P(CH_2CH_2OBu)_3]$
13. tricyanoethylphosphine, $[P(CH_2CH_2CN)_3]$
14. methyldiphenylphosphine, $[PMePh_2]$
15. triphenylphosphine, $[PPh_3]$
16. dimethylphenylphosphine, $[PMe_2Ph]$
17. diethylphenylphosphine, $[PEt_2Ph]$
18. ethylenebis(diphenylphosphiine), $[Ph_2PCH_2CH_2PPh_2]$
19. methylenebis(diphenylphosphine), $[Ph_2PCH_2PPh_2]$
20. propylenebis(diphenylphosphine), $[Ph_2PCH_2CH_2CH_2PPh_2]$
21. ethylenebis(dicyclopentylphosphine), $[(C_5H_9)_2PCH_2CH_2P(C_5H_9)_2]$
22. methylenebis(dicyclopentylphosphine), $[(C_5H_9)_2PCH_2P(C_5H_9)_2]$
23. propylenebis(dicyclopentylphosphine), $[(C_5H_9)_2PCH_2CH_2CH_2P(C_5H_9)_2]$
24. ethylenebis(dicyclohexylphosphine), $[(C_6H_{11})_2PCH_2CH_2P(C_6H_{11})_2]$
25. methylenebis(dicyclohexylphosphine), $[(C_6H_{11})_2PCH_2P(C_6H_{11})_2]$
26. propylenebis(dicyclohexylphosphine), $[(C_6H_{11})_2PCH_2CH_2CH_2P(C_6H_{11})_2]$ A preferable imidazolium-2-ylidene compound includes, for example, imidazoline-2-ylidene derivatives and 4,5-dihydroimidazoline-2-ylidene derivatives, and specifically, an N,N'-dimesitylimidazoline-2-ylidene ligand and an N,N'-dimesityl-4,5-dihydroimidazoline-2-ylidene ligand.

4. Organometallic Compounds and Manufacturing Method Thereof.

The organometallic compound, a target product of the present invention, is manufactured by the first manufacturing method wherein a starting substance comprising a zero-valent transition metal complex (A) is reacted with a compound (B) shown by the above described general formula (1) and a neutral ligand (C) in one step, or by the second manufacturing method wherein a high-valent transition metal complex (A') is reacted with a compound (B') shown by the above-described general formula (4) and a neutral ligand (C') in one step under reducing condition.

Therefore, the above-described organometallic compound is not particularly limited as long as it is the one obtained by the first or the second manufacturing method, but a compound shown by the following general formula (5) or (6) is preferable:

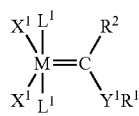 (5)

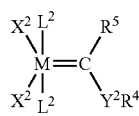 (6)

(wherein M is a transition metal element; each of $R^1$, $R^2$, $R^4$, $R^5$, $Y_1$, $Y^2$, $X^1$ and $X^2$ have each the same definition as described above. Two $L^1$s and $L^2$s may be the same or different each other, and are neutral electron donors).

Among others, a most suitable organometallic compound in view of reactivity and usefulness is, in particular, an organometallic compound wherein M is ruthenium or osmium; $R^2$ or $R^5$ is a hydrogen atom; $R^1$ or $R^4$ is a phenyl group or a phenyl group substituted with at least one substituent selected from a group consisting of an alkyl group having 1 to 5 carbon atoms, a carboxyl group, an alkoxy group having 1 to 5 carbon atoms, an alkenyloxy group having 1 to 5 carbon atoms, an aryloxy group having 6 to 10 carbon atoms, an alkylsilyl group having 1 to 6 carbon atoms, an arylsilyl group having 6 to 10 carbon atoms, an acyl group having 1 to 7 carbon atoms, a hydroxyl group, an amino group having not more than 10 carbon atoms, a halogen atom, a nitro group and an acetyl group; $Y^1$ or $Y^2$ is an oxygen atom, a sulfur atom or a selenium atom.

Further, a particularly preferable one in view of stability, usefulness and cost of a product is an organometallic compound wherein M is ruthenium; $R^2$ or $R^5$ is a hydrogen atom; $X^1$ or $X^2$ is chlorine; $Y^1$ or $Y^2$ is a sulfur atom or a selenium atom; $R^1$ or $R^4$ is a phenyl group or the above-described substituted phenyl group.

When $Y^1$ or $Y^2$ is a hetero element such as sulfur, selenium and nitrogen, an organometallic compound obtained has superior heat stability due to π-electron donating nature of these elements, and advantageous for obtaining a desired product in high yield because it enables the reaction to be conducted at high temperature.

As one of the features of a manufacturing method of the present invention, a compound (B) shown by the general formula (1) or a compound (B') shown by the general formula (4) is used as a reaction reagent. Said compounds are stable to heat or light, enabling the reaction to be conducted under various synthesis conditions.

The first or the second manufacturing method of the present invention generally comprises: adding the above-described three raw materials in a solvent, stirring, if necessary, reacting in one step at −78° C. to 150° C., preferably at −10° C. to 110° C. under nitrogen atmosphere, and after completion of the reaction, removing the solvent by evaporation, and isolating a complex by recovering and washing a solid obtained.

The above-described solvent is not particularly limited, but desirably includes, for example, toluene, benzene, methylene chloride, chloroform, methanol, ethanol, isopropanol, tetrahydrofuran, diethyl ether and acetonitrile, and in particular, in the second manufacturing method, methanol, ethanol and isopropanol are desirable.

In the first manufacturing method, as described above, reaction proceeds only by adding the above-described raw materials, and thus a reducing agent is not necessary to be added, while in the second manufacturing method, the reaction must be carried out under reducing condition by adding a reducing agent, because the reaction does not proceed only by adding the above-described raw materials.

As the above-described reducing agent, any kind of the agent can be used as long as it can reduce a polyvalent transition metal complex, but preferably a typical element or a compound containing a typical element is desirable. Specifically, zinc, sodium salts including typically sodium carbonate, metal sodium, sodium compounds such as sodium amalgam, are most suitable. In particular, in view of by-products in the reaction system or easiness of the process, a sodium salt, typically sodium carbonate, is preferable.

As described above, in the second manufacturing method, an alcoholic solvent is preferably used as a solvent, and when a solvent other than the alcoholic solvent is used, co-existence of an alcohol in the system as a reducing auxiliary is necessary.

In the second manufacturing method, an addition of a coordinative compound as a reducing auxiliary is effective to obtain a product in high yield. It is considered that these compounds exhibit a reaction promoting effect by stabilizing a zero-valent complex generated in the system.

Specific examples include, for example, phosphine derivatives, olefin derivatives, nitrile derivatives, ketone derivatives, ether derivatives, thioether derivatives and amine derivatives, and among others, olefin derivatives are preferable.

Further, in the second manufacturing method, a target organometallic compound can be obtained more efficiently by first adding to a solvent a transition metal complex (A') as a raw material, a reducing agent and a stabilizer for stabilizing a transition metal reduced, followed by removing the solvent by evaporation from a solution obtained and newly adding a solvent to react a compound (B') shown by the general formula (4) and a neutral ligand (C').

In this case, an alcoholic solvent such as methanol and ethanol is desirable as the solvent firstly used, and benzene, toluene, THF, methylene chloride, chloroform and the like are desirable as the solvent secondly used.

The stabilizer used preferably includes a neutral ligand, and more preferably includes, for example, phosphine derivatives, olefin derivatives, nitrile derivatives, ketone derivatives, ether derivatives, thioether derivatives and amine derivatives.

Typical chemical reaction schemes of the present invention are shown bellow as the schemes (7) to (15):

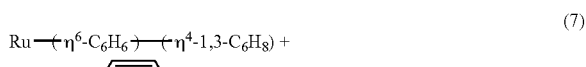

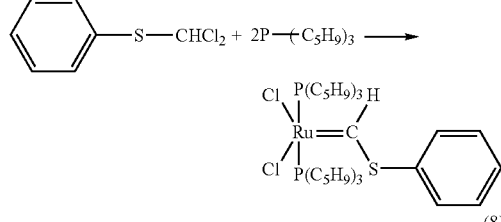

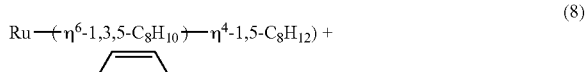

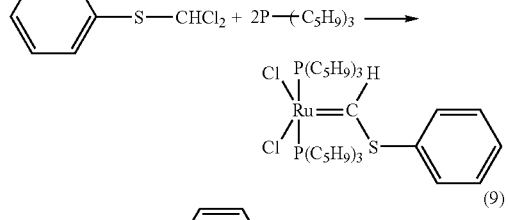

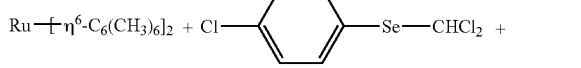

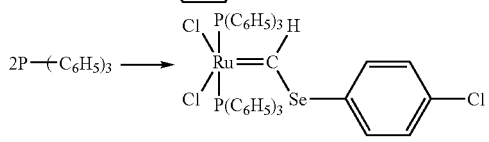

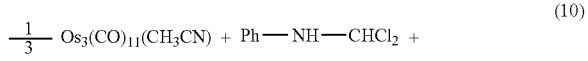

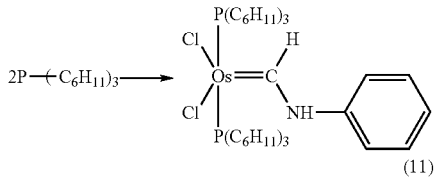

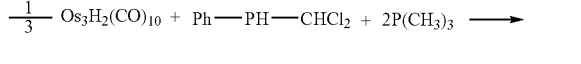

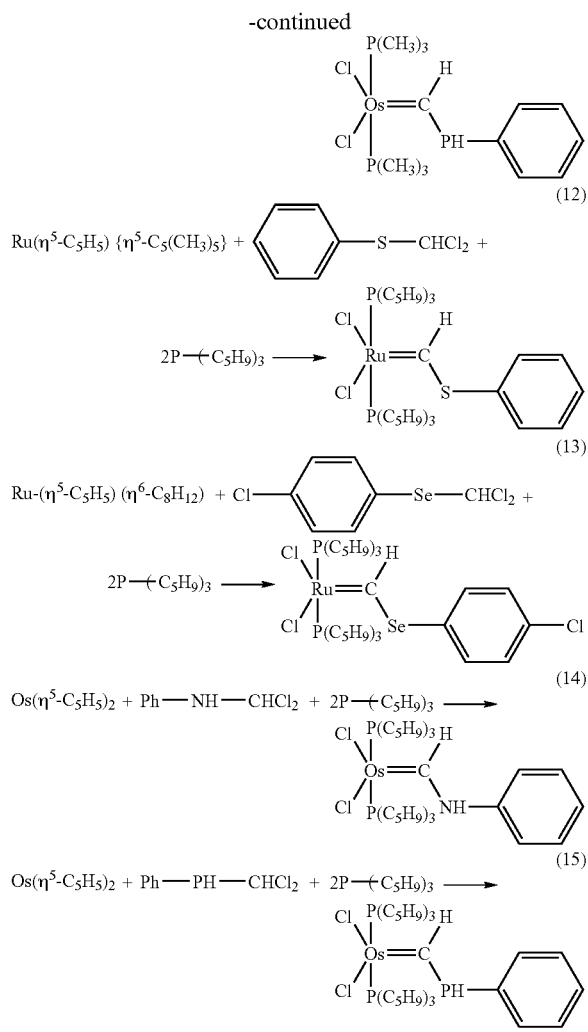

EXAMPLES

In the following, the present invention will be explained in more detail referring to Examples, but the present invention is not limited thereto by any means, and every embodiment utilizing the technical idea of the present invention should be included in the scope of the present invention.

Examples 1 to 5

To 0.006 mole of a zero-valent transition metal complex, Ru($\eta^6$-benzene)($\eta^4$-1,3-cyclohexadiene), 0.012 mole of tricyclohexylphosphine and 0.006 mole of a compound shown by the formula $R^1Y^1CHCl_2$ were added along with 20 g of benzene, and the solution was reacted in a 100 ml of flask at 50° C. for 3 hours in nitrogen gas flow. After completion of the reaction, the solvent was removed by evaporation and a solid obtained was recovered and washed to isolate an organometallic compound. The results are shown in Table 1.

In Table 1, $R^1$ and $Y^1$ correspond to $R^1$ and $Y^1$ in the above-described formula $R^1Y^1CHCl_2$, for example, and Example 1 shows that a phenyl group and a sulfur atom were used as $R^1$ and $Y^1$, respectively, that is, an organometallic compound having chemical structure of the formula (a) was obtained by using $C_6H_5$—S—$CHCl_2$.

TABLE 1

|  | $R^1$ | $Y^1$ | Yield | Organometallic compound |
|---|---|---|---|---|
| Example 1 | Ph | S | 87% | Formula (a) |
| Example 2 | p-tolyl | S | 83% | Formula (b) |
| Example 3 | p-Cl-Ph | S | 80% | Formula (c) |
| Example 4 | i-Pr | S | 85% | Formula (d) |
| Example 5 | Ph | Se | 85% | Formula (e) |

Results of Evaluation

In all of Examples 1 to 5, yield was not lower than –80%, and in particular, the yield in Example 1 was as high as 87% showing satisfactory result.

Examples 6 to 9

To 0.006 mole of a zero-valent transition metal complex, Ru($\eta^4$-1,5-cyclooctadiene)($\eta^6$-1,3,5-cyclooctatriene), 0.012 mole of tricyclohexylphosphine and 0.006 mole of a compound shown by formula $R^1Y^1CHCl_2$ were added along with 20 g of benzene, and the solution was reacted in a 100 ml of flask at 60° C. for 6 hours in nitrogen gas flow. After completion of the reaction, the solvent was removed by evaporation and a solid obtained was recovered and washed to isolate a complex. The results are shown in Table 2.

TABLE 2

|  | $R^1$ | $Y^1$ | Yield | Organometallic compound |
|---|---|---|---|---|
| Example 6 | Ph | S | 73% | Formula (a) |
| Example 7 | p-tolyl | S | 70% | Formula (b) |
| Example 8 | p-Cl-Ph | S | 67% | Formula (c) |
| Example 9 | Ph | Se | 66% | Formula (e) |

Results of Evaluation

In Examples 6 to 9, the results were satisfactory though an average yield was relatively low of about 70%.

Examples 10 to 13

To 0.006 mole of a tri-valent transition metal complex, $RuCl_3.3H_2O$, zinc (0.06 mole) as a reducing agent was added in ethanol at room temperature, followed by stirring for 30 minutes. Then, 0.012 mole of tricyclohexylphosphine and 0.006 mole of a compound shown by formula $R_4Y^2CHCl_2$ were added along with 20 g of toluene, and the solution was reacted in a 100 ml of flask at 80° C. for 6 hours in nitrogen gas flow. After completion of the reaction, the precipitate was removed by filtering and then the solvent was removed by evaporation, and a solid obtained was recovered and washed to isolate a complex. The results are shown in Table 3.

TABLE 3

|  | $R^4$ | $Y^2$ | Yield | Organometallic compound |
|---|---|---|---|---|
| Example 10 | Ph | S | 68% | Formula (a) |
| Example 11 | p-tolyl | S | 67% | Formula (b) |
| Example 12 | p-Cl-Ph | S | 73% | Formula (c) |
| Example 13 | Ph | Se | 70% | Formula (e) |

Results of Evaluation

In Examples 10 to 13, the results were satisfactory though an average yield was a little low of about 70%.

Examples 14 to 17

To 0.006 mole of a tri-valent transition metal complex, $RuCl_3 \cdot 3H_2O$, zinc (0.06 mole) as a reducing agent and 0.06 mole of 1,5-cyclooctadiene were added in ethanol, followed by stirring at room temperature for 1 hour and excess zinc was removed by filtering. The solvent was removed from the solution obtained by evaporation and the residue was re-dissolved in THF, then 0.012 mole of tricyclohexylphosphine and 0.006 mole of a compound shown by the formula $R^4Y$—$CHCl_2$ were added and the solution was reacted at 60° C. for 1 hour in nitrogen gas flow. After completion of the reaction, the solvent was removed by evaporation and the solid obtained was recovered and washed to isolate a complex. The results are shown in Table 4.

TABLE 4

| | $R^4$ | $Y^2$ | Yield | Organometallic compound |
|---|---|---|---|---|
| Example 14 | Ph | S | 88% | Formula (a) |
| Example 15 | p-tolyl | S | 77% | Formula (b) |
| Example 16 | p-Cl-Ph | S | 73% | Formula (c) |
| Example 17 | Ph | Se | 82% | Formula (e) |

In Examples 14 to 17, average yield was as high about 80%. In particular, the yields in Example 14 and Example 17 were as high as not lower than 80% showing satisfactory results.

Examples 18 to 21

To 0.006 mole of a zero-valent transition metal complex, $Ru(\eta^6$-p-cymene$)(\eta^4$-1,5-cyclooctadiene), 0.012 mole of tricyclohexylphosphine and 0.006 mole of a compound shown by the formula $R^1Y^1CHCl_2$ were added along with 20 g of toluene, and the solution was reacted in a 100 ml of flask at 60° C. for 12 hours in nitrogen gas flow. After completion of the reaction, the solvent was removed by evaporation and the solid obtained was recovered and washed to isolate an organometallic compound. The result are shown in Table 5.

TABLE 5

| | $R^1$ | $Y^1$ | Yield | Organometallic compound |
|---|---|---|---|---|
| Example 18 | Ph | S | 91% | Formula (a) |
| Example 19 | p-Me-Ph | S | 87% | Formula (b) |
| Example 20 | Cy | S | 88% | Formula (f) |
| Example 21 | Ph | Se | 82% | Formula (e) |

Results of Evaluation

In all of Examples 18 to 21, yields were not lower than 80%, and in particular, the yield in Example 18 was as high as 91% showing satisfactory result.

Examples 22 to 23

To a tri-valent transition metal complex, $RuCl_3 \cdot 3H_2O$ (0.006 mole), sodium carbonate (0.06 mole) as a reducing agent, tricyclohexylphosphine (0.012 mole) and a compound (0.006 mole) shown by the formula $R^4Y^2CHCl_2$, further cyclooctadiene (0.06 mole) as a reducing auxiliary, were added in ethanol (20 ml), and the solution was reacted in a 100 ml of flask at 60° C. for 6 hours in nitrogen gas flow. After completion of the reaction, the precipitate was removed by filtering and then the solvent was removed by evaporation, and the solid obtained was recovered and washed to isolate a complex. The results are shown in Table 6.

Examples 24 to 25

To a di-valent transition metal complex, $[RuCl_2\{\eta^6$—$CH(CH_3)_2C_6H_4CH_3\}]_2$(0.006 mole), sodium carbonate (0.06 mole) as a reducing agent, tricyclohexylphosphine (0.012 mole) and a compound (0.006 mole) shown by formula $R^4Y^2CHCl_2$, and further ethanol (1 ml) as a reducing auxiliary, were added in toluene (20 ml), and the solution was reacted in a 100 ml of flask at 60° C. for 6 hours in nitrogen gas flow. After completion of the reaction, the precipitate was removed by filtering and then the solvent was removed by evaporation, and the solid obtained was recovered and washed to isolate a complex. The results are shown in Table 6;

TABLE 6

| | $R^4$ | $Y^2$ | Yield | Organometallic compound |
|---|---|---|---|---|
| Example 22 | Ph | S | 82% | Formula (a) |
| Example 23 | p-Me-Ph | S | 81% | Formula (b) |
| Example 24 | Ph | S | 84% | Formula (a) |
| Example 25 | p-Me-Ph | S | 78% | Formula (b) |

Results of Evaluation

In Examples 22 to 25, average yield was not lower than 80%, and thus the effects of the reducing auxiliaries were confirmed.

Examples 26 to 30

To a zero-valent transition metal complex, $Ru(\eta^6$-p-cymene$)(\eta^4$-1,5-cyclooctadiene) (0.006 mole), 0.012 mole of a neutral ligand and 0.006 mole of a compound shown by formula $R^1Y^1CHCl_2$ were added in 20 g of benzene, and the solution was reacted in a 100 ml of flask at 50° C. for 3 hours in nitrogen gas flow. After completion of the reaction, the solvent was removed by evaporation, and the solid obtained was recovered and washed to isolate an organometallic compound. The results are shown in Table 7.

In Table 7, the data in Examples 18 to 21 obtained under the similar conditions were listed again as comparative references.

TABLE 7

| | $R^1$ | $Y^1$ | Neutral ligand | Yield | Organometallic compound |
|---|---|---|---|---|---|
| Example 18 | Ph | S | $PCy_3$ | 91% | Formula (a) |
| Example 19 | p-Me-Ph | S | $PCy_3$ | 87% | Formula (b) |
| Example 20 | Cy | S | $PCy_3$ | 88% | Formula (f) |
| Example 21 | Ph | Se | $PCy_3$ | 82% | Formula (e) |
| Example 26 | p-Cl-Ph | S | $PCy_3$ | 70% | Formula (c) |
| Example 27 | p-MeO-Ph | S | $PCy_3$ | 80% | Formula (g) |
| Example 28 | Ph | S | IMes | 35% | Formula (h) |
| Example 29 | N(carbazole) | N | $PCy_3$ | 45% | Formula (i) |
| Example 30 | N(pyrrolidinone) | N | $PCy_3$ | 48% | Formula (j) |

Cy = Cyclohexyl group
$PCy_3$ = Tricyclohexylphosphine
IMes = N,N'-Dimesitylimidazolium-2-ylidene Results of Evaluation In Examples 18 to 21 and Example 27, yields were not lower than 80% showing satisfactory results. Even in Example 26, the formation was confirmed in about 70% yield. While, in Examples 28 to 30, although yields were not so high, it was meaningful that synthesis of the product wherein a neutral ligand is imidazolium-2-ylidene ligand or Y is nitrogen was confirmed.

Examples 31 to 33

Experiments were conducted using different kinds of zero-valent transition metal complexes. To 0.006 mole of a zero-valent transition metal complex, 0.012 mole of a neutral ligand ($PCy_3$=tricyclohexylphosphine) and 0.006 mole of a compound shown by formula $R^1Y^1CHCl_2$ ($PhSCHCl_2$) were added in 20 g of benzene, and the solution was reacted in a 100 ml of flask at the temperatures and the times as shown in Table 8 in nitrogen gas flow. After completion of each reaction, the solvent was removed by evaporation, and the solid obtained was recovered and washed to isolate each organometallic compound (all compounds are shown by formula (a)). The results are shown in Table 8.

In Table 8, the data in Examples 1, 6 and 18, obtained under the similar conditions were listed again as comparative references.

TABLE 8

| | Zero-valent transition metal complex | Reaction temp. | Reaction time | Yield | Organometallic compound |
|---|---|---|---|---|---|
| Example 1 | Ru(benzene)(chd) | 50° C. | 3 h | 87% | Formula (a) |
| Example 6 | Ru(cod)(cot) | 60° C. | 6 h | 73% | Formula (a) |
| Example 18 | Ru(p-cymene)(cod) | 60° C. | 12 h | 91% | Formula (a) |
| Example 31 | Ru(benzene)(cod) | 60° C. | 12 h | 74% | Formula (a) |
| Example 32 | Ru(p-cymene)(chd) | 60° C. | 12 h | 68% | Formula (a) |
| Example 33 | Ru(naphthalene)(cod) | 40° C. | 12 h | 73% | Formula (a) | chd = 1,3-cyclohexadiene
cod = 1,5-cyclooctadiene
cot = 1,3,5-cyclooctatriene

Results of Evaluation

It was confirmed that target products could be obtained in high yield using various zero-valent complexes. In particular in Example 18, the target product was obtained in such high yield as 91% showing very satisfactory result. Further, synthesis yields of these zero-valent complexes themselves were as follows, and Example 18 was confirmed to be a very good precursor in view of synthesis yield.

| Name of zero-valent complex | Synthesis yield | Example used |
|---|---|---|
| Ru(benzene)(chd) | 61% | Example 1 |
| Ru(cod)(cot) | 82% | Example 6 |
| Ru(p-cymene)(cod) | 91% | Example 18 |
| Ru(benzene)(cod) | 66% | Example 31 |
| Ru(p-cymene)(chd) | 20% | Example 32 |
| Ru(naphthalene)(cod) | 50% | Example 33 |

Examples 34

To 1.3 mmole of a zero-valent transition metal complex, Ru($\eta^6$-p-cymene)($\eta^4$-1,5-cyclooctadiene), 2.59 mmole of tricyclohexylphosphine and 1.3 mmole of $PhSCHCl_2$ were added in 10 ml of benzene, and the solution was reacted in a 30 ml of round bottom flask at 60° C. for 12 hours in nitrogen gas flow. After completion of the reaction, the solvent was removed by evaporation and the solid obtained was recovered to isolate dichloro[bis(tricyclohexylphosphino)]phenylthiomethyno-ruthenium in 93% yield. Using 0.02 mmole of the complex obtained, 20 mmole of norbornene in 100 ml of a toluene solution was polymerized in 200 ml of Schrenk flask at room temperature for 1 hour. The results are shown in Table 9.

Examples 35

A complex was obtained by washing 1 mmole of dichloro [bis(tricyclohexylphosphino)]phenylthiomethyno-ruthenium obtained in Example 34 with 10 ml of methanol at −78° C., then drying and recovering. Using this complex, norbornene was polymerized similarly as in Example 34.
The results are shown in Table 9.

Comparative Example 1

In accordance with the synthesis method described in "Organometallics", 2002, 21, 2153–2164, dichloro[bis(tricyclohexylphosphino)]phenylthiomethyno-ruthenium was synthesized, and a complex was isolated by removing the solvent similarly as in Example 34 without recrystallization. Using this complex, norbornene was polymerized similarly as in Example 34. The results are shown in Table 9.

Comparative Examples 2 and 3

A solid was obtained by washing 1 mmole of the complex obtained in Comparative Example 1 with 10 ml of methanol at −78° C. similarly as in Example 35, followed by drying and recovering. Using this solid, norbornene was polymerized similarly as in Example 34 (Comparative Example 2). The rest of the complex was rewashed with 10 ml of methanol at −78° C., followed by drying to recover a solid. Using this solid, norbornene was polymerized similarly as in Example 34 (Comparative Example 3). The results are shown in Table 9.

TABLE 9

| | Methanol washing | Recovery ratio of organometallic compound after washing | Presence of monomer | Yield of polymerization | Mn |
|---|---|---|---|---|---|
| Example 34 | None | As crude product | No | >99% | 200,000 |
| Example 35 | Once | 90% | No | >99% | 200,000 |
| Comparative Example 1 | None | As crude product | Yes | 68% | 50,000 |
| Comparative Example 2 | Once | 90% | Reduced amount | 75% | 130,000 |
| Comparative Example 3 | Twice | 81% | Further reduced amount | 88% | 150,000 |

Results of Evaluation

In Example 34, only the solvent was removed from the product obtained, (clichloro[bis(tricyclohexylphosphino)] phenylthiomethynoruthenium), without washing with methanol, but yield of polynorbornene was not lower than 99% showing very superior result.

In Example 35, the solvent was removed from the product obtained, (dichloro[bis(tricyclohexylphosphino)]phenylthiomethynoruthenium), by washing with methanol, but yield of polynorbornene was not lower than 99% and about the same level as in Example 34. This means that the product of the present invention, dichloro[bis(tricyclohexylphosphino)]phenylthiomethynoruthenium provides polynorbornene in very high yield even without washing with methanol, showing very superior compared to the yield of 68% by the conventional method in Comparative Example 1.

While, in Comparative Example 1, the product was used as it is as a polymerization catalyst of norbornene, and the polymerization yield was very low of 68%. The reason is considered to be much amount of residual monomers present in the product, which inhibits the polymerization.

Also in Comparative Example 2, the product was washed once with methanol, and the polymerization yield was far inferior compared to that in Example 34, although it was increased from 68% to 75%. This is because recovery rate in washing was 90% and some amount of the complex was lost during removal of impurity such as some amount of monomers. This result is an evidence of high superiority of the present invention compared to the conventional technology.

In Comparative Example 3, the product was washed twice with methanol, but the polymerization yield was inferior at about 11% of the rate in Example 34, although it was increased from 68% to 88%. This is because recovery rate in washing was 81% and around 20% of the complex was lost during removal of impurities such as some amount of monomers. This result is an evidence of high superiority of the present invention compared to the conventional technology.

Chemical formulas of organometallic compounds (a) to (j) obtained in Examples 1 to 30 are shown bellow.

(a)
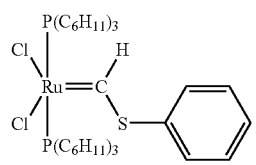

(b)
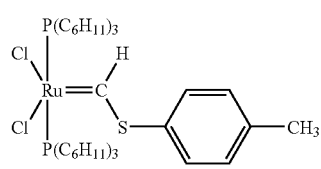

(c)
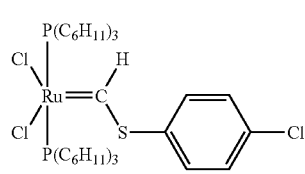

(d)
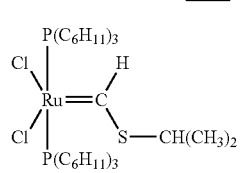

-continued (e)
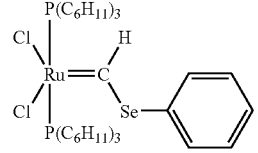

(f)
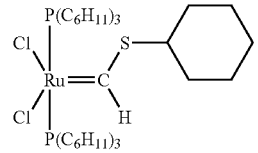

(g)
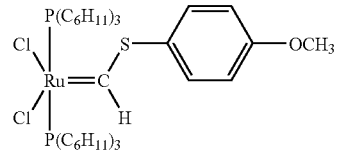

(h)
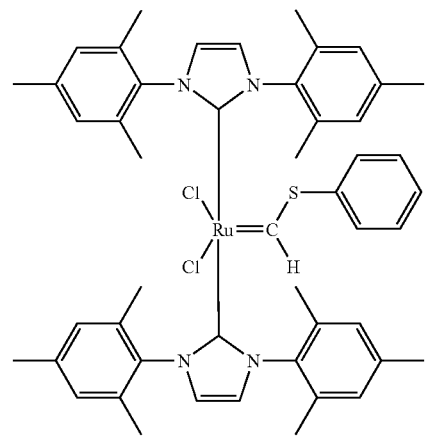

(i)
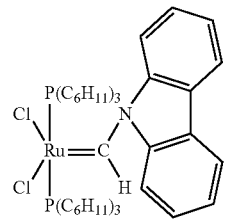

(j)
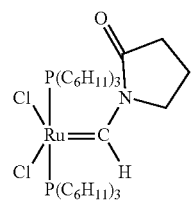

According to the present invention, an organometallic compound usefully utilized as a catalyst for polyolefin manufacturing by ring-opening metathesis polymerization of an olefin having strain in a molecule such as dicyclopentadiene or synthesis of epothilones by ring-closing metathesis reactions can be synthesized efficiently and at a low cost using a starting material which is easily available due to relatively simple chemical structure. Thus, the present invention is useful.

The present invention also enables to simply isolate an organometallic compound with high activity from a reaction solution without any possibility of co-existence of a vinyl-hetero compound or a vinyl compound exchanged in a system, which tends to accompany as an impurity in conventional methods, and thus has an effect to provide very high polymerization yield when a norbornene type monomer is polymerized using this compound as a polymerization catalyst.

What is claimed is:

1. A method for synthesizing an organometallic compound comprising: reacting, in one step, a starting material having a zero-valent transition metal complex (A), a compound (B) shown by the following general formula (1) and a neutral ligand (C):

$$R^1Y^1CR^2X^1_2 \tag{1}$$

wherein $R^1$ is a hydrogen atom, an alkyl group having 1 to 20 carbon atoms, an alkenyl group having 2 to 20 carbon atoms or an aryl group having 6 to 20 carbon atoms, which may be substituted with an alkyl group having 1 to 5 carbon atoms, a carboxyl group, an alkoxy group having 1 to 5 carbon atoms, an alkenyloxy group having 1 to 5 carbon atoms, an aryloxy group having 6 to 10 carbon atoms, an alkylsilyl group having 1 to 6 carbon atoms, an arylsilyl group having 6 to 10 carbon atoms, an acyl group having 1 to 7 carbon atoms, a hydroxyl group, an amino group having 0 to 10 carbon atoms, a halogen atom, a nitro group, an acetyl group or an acetoxy group; $Y^1$ is a chalcogen atom or a nitrogen-containing group shown by the following formula (2):

(2)

or a phosphorus-containing group shown by the following formula (3):

(3)

$X^1$ is a halogen atom; $R^2$ and $R^3$ in the formula have the same definition as $R^1$, and any pair of $R^1$, $R^2$ and $R^3$ may be bonded each other.

2. A method for synthesizing an organometallic compound comprising: reacting, in one step under reducing condition, a starting material having a polyvalent transition metal complex (A'), a compound (B') shown by the following general formula (4) and a neutral ligand (C'):

$$R^4Y^2CR^5X^2_2 \tag{4}$$

wherein $R^4$ is a hydrogen atom, an alkyl group having 1 to 20 carbon atoms, an alkenyl group having 2 to 20 carbon atoms or an aryl group having 6 to 20 carbon atoms, which may be substituted with an alkyl group having 1 to 5 carbon atoms, a carboxyl group, an alkoxy group having 1 to 5 carbon atoms, an alkenyloxy group having 1 to 5 carbon atoms, an aryloxy group having 6 to 10 carbon atoms, an alkylsilyl group having 1 to 6 carbon atoms, an arylsilyl group having 6 to 10 carbon atoms, an acyl group having 1 to 7 carbon atoms, a hydroxyl group, an amino group having 0 to 10 carbon atoms, a halogen atom, a nitro group, an acetyl group or an acetoxy group; $Y^2$ is a chalcogen atom or a nitrogen-containing group shown by the following formula (2):

(2)

or a phosphorus-containing group shown by the following formula (3):

(3)

$X^2$ is a halogen atom; $R^5$ and $R^3$ in the formula have the same definition as $R^4$, and any pair of $R^3$, $R^4$ and $R^5$ may be bonded each other.

3. The method for synthesizing an organometallic compound according to claim 1, characterized by that said transition metal complex (A) has an arene ligand and an olefin ligand.

4. The method for synthesizing an organometallic compound according to claim 3, characterized by that said olefin ligand is a cyclic olefin ligand.

5. The method for synthesizing an organometallic compound according to claim 2, characterized by that said transition metal complex (A') has an arene ligand.

6. The method for synthesizing an organometallic compound according to claim 1 or 2, characterized by that a central metal of said transition metal complex (A) or (A') is a transition metal of VIA group, VIIA group, VIII group or IB group.

7. The method for synthesizing an organometallic compound according to claim 6, characterized by that a central metal of said transition metal complex (A) or (A') is ruthenium or osmium.

8. The method for synthesizing an organometallic compound according to claim 1 or 2, characterized by that $R^2$ or $R^5$ in said formula is a hydrogen atom.

9. The method for synthesizing an organometallic compound according to claim 1 or 2, characterized by that $R^1$, $R^3$ or $R^4$ in said formula is a phenyl group or a phenyl group substituted with at least one substituent selected from a group consisting of an alkyl group having 1 to 5 carbon atoms, a carboxyl group, an alkoxy group having 1 to 5 carbon atoms, an alkenyloxy group having 1 to 5 carbon atoms, an aryloxy group having 6 to 10 carbon atoms, an alkylsilyl group having 1 to 6 carbon atoms, an arylsilyl group having 6 to 10 carbon atoms, an acyl group having 1 to 7 carbon atoms, a hydroxyl group, an amino group having not more than 10 carbon atoms, a halogen atom, a nitro group and an acetyl group.

10. The method for synthesizing an organometallic compound according to claim 1 or 2, characterized by that $Y^1$ or $Y^2$ in said formula is an oxygen atom, a sulfur atom or a selenium atom.

11. The method for synthesizing an organometallic compound according to claim 1 or 2, characterized by that a neutral ligand (C) or (C') is a tertiary phosphine or an imidazolium-2-ylidene compound.

12. The method for synthesizing an organometallic compound according to claim 2, characterized by that said reducing condition is realized by using a reducing agent.

13. The method for synthesizing an organometallic compound according to claim 12, characterized by that said reducing agent is a typical element or a compound containing the typical element.

14. The method for synthesizing an organometallic compound according to claim 13, characterized by that said reducing agent is zinc.

15. The method for synthesizing an organometallic compound according to claim 13, characterized by that said reducing agent is a sodium compound.

16. The method for synthesizing an organometallic compound according to claim 2, characterized by that an alcohol further coexists as a reducing auxiliary.

17. The method for synthesizing an organometallic compound according to claim 2, characterized by that an olefin compound further coexists as a reducing auxiliary.

18. The method for synthesizing an organometallic compound according to claim 17, characterized by that said olefin compound is a cyclic olefin.

19. The method for synthesizing an organometallic compound according to claim 1, characterized by that said organometallic compound is a compound shown by the following general formula (5):

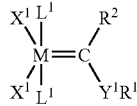
(5)

wherein M is a transition metal element; $R^1$, $R^2$, $Y^1$ and $X^1$ have each the same definition as described in claim 1 and wherein the two $L^1$s may be the same or different each other and are neutral electron donors.

20. The method for synthesizing an organometallic compound according to claim 2, characterized by that said organometallic compound is a compound shown by the following general formula (6):

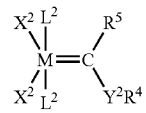
(6)

wherein M is a transition metal element; $R^4$, $R^5$, $Y^2$ and $X^2$ have each the same definition as described in claim 2 and wherein the two $L^2$s may be the same or different each other and are neutral electron donors.

21. The method for synthesizing an organometallic compound according to claim 19 or 20, characterized by that M in said formula is ruthenium or osmium.

22. The method for synthesizing an organometallic compound according to claim 19 or 20, characterized by that $R^2$ or $R^5$ in said formula is a hydrogen atom.

23. The method for synthesizing an organometallic compound according to claim 19 or 20, characterized by that $R^1$, $R^3$ or $R^4$ in said formula is a phenyl group or a phenyl group substituted with at least one substituent selected from a group consisting of an alkyl group having 1 to 5 carbon atoms, a carboxyl group, an alkoxy group having 1 to 5 carbon atoms, an alkenyloxy group having 1 to 5 carbon atoms, an aryloxy group having 6 to 10 carbon atoms, an alkylsilyl group having 1 to 6 carbon atoms, an arylsilyl group having 6 to 10 carbon atoms, an acyl group having 1 to 7 carbon atoms, a hydroxyl group, an amino group having not more than 10 carbon atoms, a halogen atom, a nitro group and an acetyl group.

24. The method for synthesizing an organometallic compound according to claim 19 or 20, characterized by that $Y^1$ or $Y^2$ in said formula is an oxygen atom, a sulfur atom or a selenium atom.

25. The method for synthesizing an organometallic compound according to claim 1, characterized by that said organometallic compound is dichloro[bis(tricyclohexylphosphino)]phenylthiomethyno-ruthenium.

26. The method for synthesizing an organometallic compound according to claim 1, characterized by that said zero-valent transition metal complex (A) is ($\eta^6$-p-cymene)($\eta^4$-1,5-cyclooctadiene)ruthenium(0).

27. The method for synthesizing an organometallic compound according to claim 1, characterized by that said organometallic compound does not contain an impurity of a vinylhetero compound or a vinyl compound.

* * * * *